United States Patent
Fey et al.

(10) Patent No.: US 11,760,737 B2
(45) Date of Patent: Sep. 19, 2023

(54) PROCESS FOR MANUFACTURING 4-(2,2,3,3-TETRAFLUOROPROPYL) MORPHOLINE

(71) Applicant: Adverio Pharma GmbH, Leverkusen (DE)

(72) Inventors: Peter Fey, Wuppertal (DE); Sergii Pazenok, Leichlingen (DE); Christian Funke, Leichlingen (DE); Natalya Pavlovna Kolesnik, Kiew (UA); Olexandr Ivanovich Guzyr, Kiew (UA); Yuriy Grigorievich Shermolovich, Kiew (UA)

(73) Assignee: ADVERIO PHARM GmbH, Leverkusen (DE)

( * ) Notice: Subject to any disclaimer, the term of this patent is extended or adjusted under 35 U.S.C. 154(b) by 223 days.

(21) Appl. No.: 17/424,866

(22) PCT Filed: Jan. 15, 2020

(86) PCT No.: PCT/EP2020/050928
§ 371 (c)(1),
(2) Date: Jul. 21, 2021

(87) PCT Pub. No.: WO2020/152010
PCT Pub. Date: Jul. 30, 2020

(65) Prior Publication Data
US 2022/0089554 A1    Mar. 24, 2022

(30) Foreign Application Priority Data
Jan. 22, 2019    (EP) .................................. 19153061

(51) Int. Cl.
*C07D 265/30*    (2006.01)
*C07D 295/067*    (2006.01)

(52) U.S. Cl.
CPC .............................. *C07D 295/067* (2013.01)

(58) Field of Classification Search
CPC ........................ C07D 265/30; C07D 295/067
See application file for complete search history.

(56) References Cited

U.S. PATENT DOCUMENTS

2013/0143900 A1    6/2013    Fey

FOREIGN PATENT DOCUMENTS

| WO | 2005018568 A2 | 3/2005 |
| WO | 2013076168 A1 | 5/2013 |

OTHER PUBLICATIONS

Cohen, W.V., "Nucleophilic Substitution in Fluoroalkyl Sulfates, Sulfonates, and Related Compounds," Journal of Organic Chemistry, 1961, vol. 26., 4021-4026.
Markovskii, L.N. et al., "Reactions of Pentakis (2,2,3,3-Tetrafluoropropoxy)Phosphorane with Secondary Amines," Journal of General Chemistry USSR, Consultants Bureau, Institute of Organic Chemistry, Apr. 1980, vol. 50, No. 4, pp. 826-829.
International Search Report and Written Opinion of PCT/EP2020/050928 (filed by Adverio Pharma GmbH dated Jan. 15, 2021, entitled "Process for Manufacturing 4-(2,2,3,3-tetrafluoropropyl)morpholine"), search completed Feb. 13, 2020, mailed by the European Patent Office dated Feb. 26, 2020, 10 pages.

*Primary Examiner* — Brenda L Coleman
(74) *Attorney, Agent, or Firm* — Quarles & Brady LLP

(57) ABSTRACT

The present application relates to a novel, cost-saving and efficient process for preparing 4-(2,2,3,3-tetrafluoropropyl)morpholine which serves as an intermediate for production of medicaments and for production of medicaments for treatment and/or prophylaxis of cardiovascular disorders.

10 Claims, No Drawings

PROCESS FOR MANUFACTURING 4-(2,2,3,3-TETRAFLUOROPROPYL) MORPHOLINE

This application is a U.S. national stage entry under 35 U.S.C. § 371 for International Application No. PCT/EP2020/050928, filed Jan. 15, 2020, the contents of which are incorporated herein by reference in its entirety, which claims priority to European Patent Application No. 19153061.7, filed Jan. 22, 2019.

The present application relates to a novel and efficient process for preparing 4-(2,2,3,3-tetrafluoropropyl)morpholine which serves as an intermediate for production of medicaments and for production of medicaments for treatment and/or prophylaxis of cardiovascular disorders. 4-(2,2,3,3-tetrafluoropropyl)morpholine is an important intermediate for the synthesis of substituted 5-fluoro-1H-pyrazolopyridines which are valuable pre-cursors for the production of medicaments for the treatment of cardiovascular disorders, as described in WO 2013/076168.

The synthesis of 4-(2,2,3,3-tetrafluoropropyl)morpholine as described in WO 2013/076168 and shown in Scheme 1 below, comprises a reaction of morpholine with 2,2,3,3,-tetrafluoropropyl trifluormethansulphonate of the formula (XII). 2,2,3,3,-tetrafluoropropyl trifluormethansulphonate, being prepared from triflic anhydride (trifluoromethanesulphonic anhydride) of the formula (X), is very expensive. This is even more relevant, since in the preparation of 2,2,3,3,-tetrafluoropropyl trifluormethansulphonate of the formula (XII) one equivalent of free triflic acid (trifluoromethanesulfonic acid) per equivalent of triflic anhydride is formed as waste, which has to be removed and disposed of. Moreover, upon alkylation of morpholine with 2,2,3,3-tetrafluoropropyltrifluoromethanesulphonate, a further equivalent of the triflic acid (trifluoromethanesulfonic acid) is released. This causes a problem with waste treatment, since trifluoromethanesulfonic acid is one of the strongest acids, which, upon skin contact, causes severe burns with delayed tissue destruction, and upon inhalation causes fatal spasms, inflammation and edema.

The synthesis as described in WO 2013/076168 is illustrated in Scheme 1.

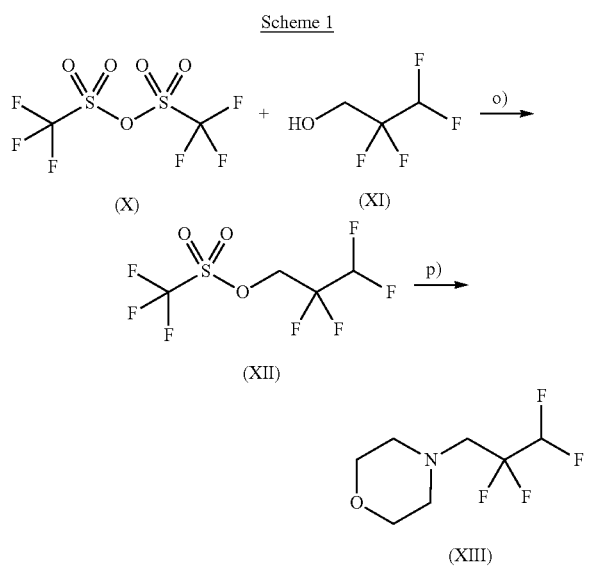

[o) without solvent; p) dichloromethane or without solvent, morpholine]

It is an object of the present invention to provide an efficient and cost-saving process with high yield for the preparation of 4-(2,2,3,3)-tetrafluoropropylmorpholine of the formula (I)

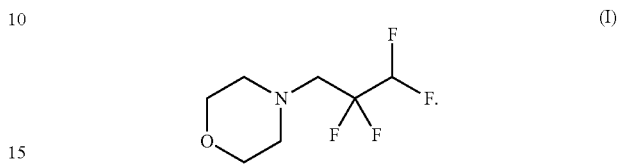

This object is achieved in accordance with the present invention, as follows.

Process for preparing a compound of the formula (I)

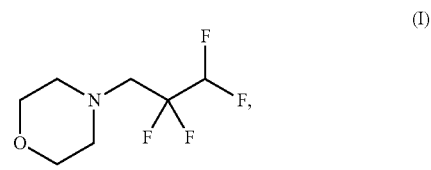 [SMILES: FC(F)C(F)(F)CN1CCOCC1]

wherein a compound of the formula (IIa)

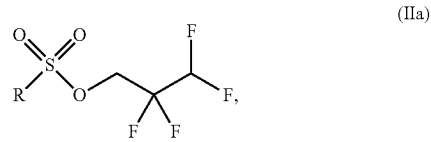

wherein

R represents $C_1$-$C_4$ alkyl, phenyl, or naphthyl,
  where the phenyl is unsubstituted or substituted by one, two or three substituents independently of one another selected from the group consisting of linear or branched $C_1$-$C_4$ alkyl, chlorine, fluorine, bromine, amino, nitro, methylsulfonyl, (dimethyl-oxopropyl)amino, and sulfonic acid 2,2,3,3-tetrafluoropropylester, is reacted without solvent with morpholine of the formula (III)

in a molar ratio of (IIa) to (III) of 1 to 2-5, in a sealed vessel or flow reactor under autogenic pressure or at 1 to 50 bar, at a temperature of 100-170° C. to give the compound of the formula (I)

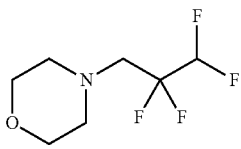

and a compound of the formula (IVa)

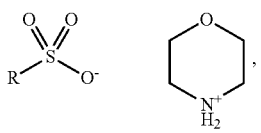

wherein

R is as defined for the compounds of the formula (IIa).

In case that R is phenyl and phenyl is substituted by one, two or three sulfonic acid 2,2,3,3-tetrafluoropropylester substituents, the sulfonic acid 2,2,3,3-tetrafluoropropylester substituent may alternatively be named —$SO_2$—O—$CH_2$—$CF_2$—$CHF_2$.

Scheme 2 below illustrates the individual reaction steps by way of example.

Scheme 2

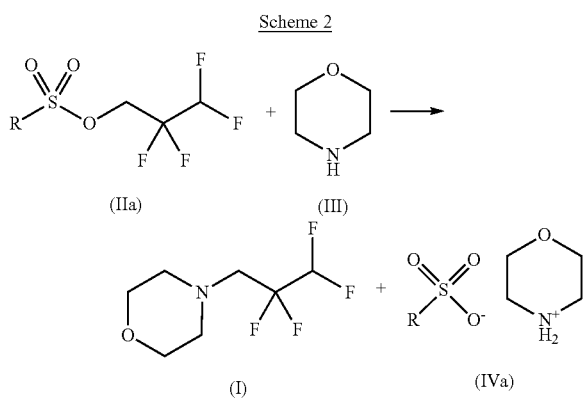

According to another embodiment of the invention, in the compound of the formula (IIa)

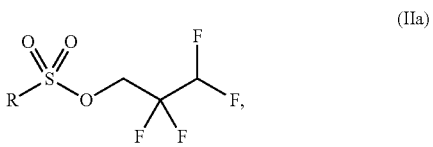

R represents methyl or phenyl,
    where the phenyl is unsubstituted or substituted by one, two or three substituents independently of one another selected from the group consisting of methyl, chlorine, amino, methylsulfonyl, and sulfonic acid 2,2,3,3-tetrafluoropropylester.

According to another embodiment of the invention, the compound of the formula (IIa)

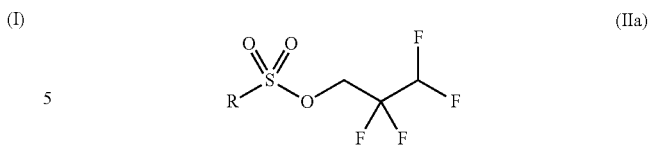

is selected from the group consisting of 1-Propanol-2,2,3,3-tetrafluoro-1-methanesulfonate, Ethanesulfonic acid-2,2,3,3-tetrafluoropropylester, 1-Propanol-2,2,3,3-tetrafluoro-1-benzenesulfonate, 1-Propanol-2,2,3,3-tetrafluoro-1-(4-methylbenzenesulfonate), Benzenesulfonic acid 4-ethyl-2,2,3,3-tetrafluoropropylester, Benzenesulfonic acid 3-methyl-2,2,3,3-tetrafluoropropylester, Benzenesulfonic acid 4-chloro-2,2,3,3-tetrafluoropropylester, Benzenesulfonic acid 3-chloro-2,2,3,3-tetrafluoropropylester, Benzenesulfonic acid 2-chloro-2,2,3,3-tetrafluoropropylester, Benzenesulfonic acid 3,5-dichloro-2,2,3,3-tetrafluoropropylester, Benzenesulfonic acid 2,6-dichloro-2,2,3,3-tetrafluoropropylester, Benzenesulfonic acid 4-fluoro-2,2,3,3-tetrafluoropropylester, Benzenesulfonic acid 3-fluoro-2,2,3,3-tetrafluoropropylester, Benzenesulfonic acid 2-fluoro-2,2,3,3-tetrafluoropropylester, Benzenesulfonic acid 2,4,5-trifluoro-2,2,3,3-tetrafluoropropylester, Benzenesulfonic acid 4-bromo-2,2,3,3-tetrafluoropropylester, Benzenesulfonic acid 3-bromo-2,2,3,3-tetrafluoropropylester, Benzenesulfonic acid 2-bromo-2,2,3,3-tetrafluoropropylester, Benzenesulfonic acid 4-bromo-2-chloro-2,2,3,3-tetrafluoropropylester, Benzenesulfonic acid 4-chloro-2-fluoro-2,2,3,3-tetrafluoropropylester, Benzenesulfonic acid 4-bromo-3-methyl-2,2,3,3-tetrafluoropropylester, Benzenesulfonic acid 4-bromo-2,6-dichloro-2,2,3,3-tetrafluoropropylester, Benzenesulfonic acid 4-amino-2,2,3,3-tetrafluoropropylester, Benzenesulfonic acid 4-(1-methylpropyl)-2,2,3,3-tetrafluoropropylester, Benzenesulfonic acid 4-(1,1 dimethylethyl)-2,2,3,3-tetrafluoropropylester, Benzenesulfonic acid 2,4-dimethyl-2,2,3,3-tetrafluoropropylester, Benzenesulfonic acid 2,5-dimethyl-2,2,3,3-tetrafluoropropylester, Benzenesulfonic acid 2,5-dimethyl-3-(methylsulfonyl)-2,2,3,3-tetrafluoropropylester, Benzenesulfonic acid 4-[(2,2-dimethyl-1-oxopropyl)amino]-2,2,3,3-tetrafluoropropylester, Benzenesulfonic acid 4-nitro-2,2,3,3-tetrafluoropropylester, Benzenesulfonic acid 2-nitro-2,2,3,3-tetrafluoropropylester, Benzenesulfonic acid 4-methyl-2-nitro-2,2,3,3-tetrafluoropropylester, Benzenesulfonic acid 2-chloro-5-nitro-2,2,3,3-tetrafluoropropylester, 1,3,5-Benzenetrisulfonic acid 2-amino-1,3,5-tris(2,2,3,3-tetrafluoropropylester, and 2-Naphthalenesulfonic acid-2,2,3,3-tetrafluoropropylester.

According to another embodiment of the invention, the compound of the formula (IIa)

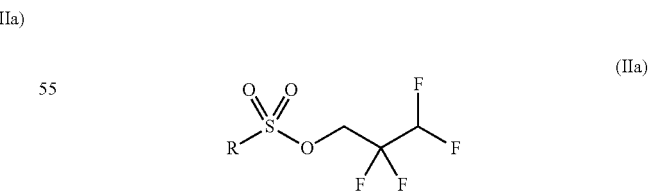

is selected from the group consisting of 1-Propanol-2,2,3,3-tetrafluoro-1-methanesulfonate, 1-Propanol-2,2,3,3-tetrafluoro-1-benzenesulfonate, 1-Propanol-2,2,3,3-tetrafluoro-1-(4-methylbenzenesulfonate), Benzenesulfonic acid 4-chloro-2,2,3,3-tetrafluoropropylester, Benzenesulfonic acid 3-chloro-2,2,3,3-tetrafluoropropylester, Benzenesulfonic acid 2-chloro-2,2,3,3-tetrafluoropropylester, Benzenesulfonic acid 3,5-dichloro-2,2,3,3-tetrafluoropropylester, Benzenesulfonic acid 2,6-dichloro-2,2,3,3-tetrafluoropylester, Benzenesulfonic acid 2,4-dimethyl-2,2,3,3-tetrafluoropropylester, Benzenesulfonic acid 2,5-dimethyl-2,2,3,3-tetrafluoropropylester, Benzenesulfonic acid 2,5-dimethyl-3-(methylsulfonyl)-2,2,3,3-tetrafluoropropylester, and 1,3,5-Benzenetrisulfonic acid 2-amino-1,3,5-tris(2,2,3,3-tetrafluoropropylester.

According to a further embodiment of the invention, the compound of the formula (I) is synthesized as follows.

Process for preparing the compound of the formula (I)

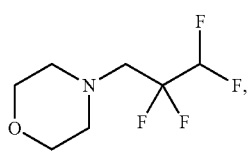
(I)

wherein the compound of the formula (II)

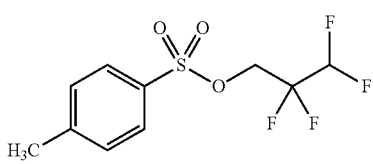
(II)

is reacted without solvent with morpholine of the formula (III)

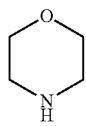
(III)

in a molar ratio of (II) to (III) of 1 to 2-5, in a sealed vessel or flow reactor under autogenic pressure or at 1 to 50 bar, at a temperature of 100-170° C. to give the compound of the formula (I)

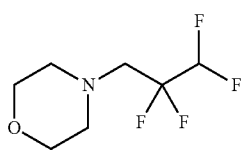
(I)

and the compound of the formula (IV).

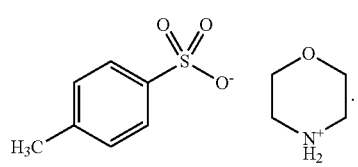
(IV)

Scheme 3 below illustrates the individual reaction steps by way of example.

Scheme 3

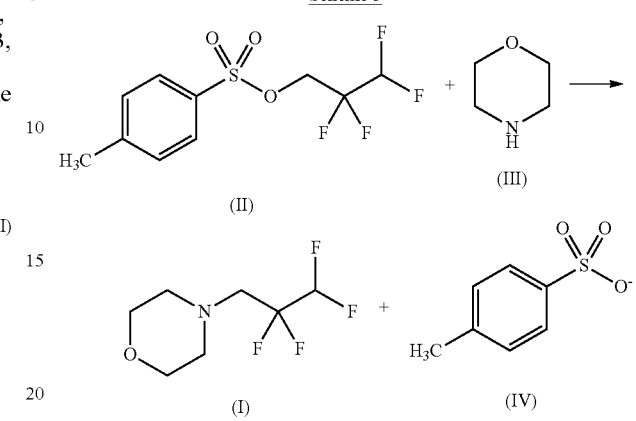

2,2,3,3-tetrafluoropropyltosylate of the formula (II) is also known as 1-Propanol-2,2,3,3-tetrafluoro-1-(4-methylbenzenesulfonate) and both names are used in an analogous manner in the present invention. WO 2005/018568 pertains to the alkylation of morpholine with a tosylate. WO 2005/018568 differs from the present invention at least in that the tosylate is not covered by formula IIa and the final product is not of formula I.

Markovskii L N, Kolesnik N P, Shermolovich, Y G., Zhurnal Obshchei Khimii (1980), 50(4), 826-9 describe a reaction of pentakis(2,2,3,3-tetrafluoropropoxy)phosphorane with secondary amines, such as morpholine. Markowskii et al. also describe a reaction of 2,2,3,3-tetrafluoropropanyl tosylate of the formula (II) with morpholine. In contrast the process according to the present invention, Markovskii et al. apply equimolar amounts of 2,2,3,3-tetrafluoropropanyl tosylate and morpholine. The reaction was conducted on a small scale in a small ampule with the goal to obtain a comparison compound for analytical purposes. The yield was only 21% which is not feasible for a synthesis on technical scale.

2,2,3,3-tetrafluoropropyltosylate of the formula (II) is considerably less reactive than 2,2,3,3,-tetrafluoropropyl trifluormethansulphonate, applied in the reaction described in WO 2013/076168, and as known from the literature even at higher temperature only a poor yield of 210% was obtained, when 2,2,3,3-tetrafluoropropyltosylate and morpholine were reacted to give 4-(2,2,3,3)-tetrafluoropropylmorpholine of the formula (I).

Therefore, it was not to be expected that according to the process of the present invention, 4-(2,2,3,3)-tetrafluoropropylmorpholine of the formula (I) could be obtained in very high yield under operationally convenient conditions by reacting a cheap and readily available 2,2,3,3-tetrafluoropropylsulfonic acid ester of the formula (IIa) or 2,2,3,3-tetrafluoropropyltosylate of the formula (II) with morpholine of the formula (III). Furthermore, it has surprisingly been found that the reaction could be operated at a very large, technically feasible scale.

2,2,3,3-tetrafluoropropyltosylate of the formula (II) is known and can be prepared according to the literature procedure, see Journal of Organic Chemistry (1961) 26, 4021-26, as illustrated in Scheme 4.

Scheme 4

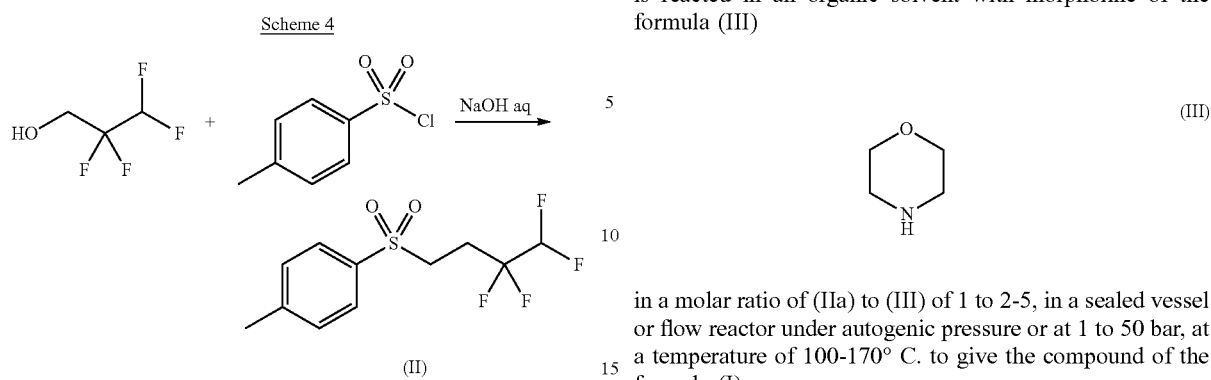

For the process according to the invention, the compound of the formula (IIa) or (II) is reacted with morpholine of the formula (III) in a molar ratio of (IIa or II) to (III) of 1 to 2-5, preferably 1 to 2.0-2.5, most preferably of 1 to 2.1. The reaction time may vary according to the batch size and reaction temperature, being selected within a range between one and up to 20 hours, preferably between 12 and up to 20 hours. If the reaction is performed at higher temperature the reaction time can be reduced.

The reaction proceeds without any solvent in the excess of morpholine.

If needed, the reaction could also be done in the presence of an organic solvent. Suitable solvents are, for example, aliphatic, alicyclic or aromatic hydrocarbons, for example petroleum ether, n-hexane, n-heptane, cyclohexane, methylcyclohexane, benzene, toluene, xylene or decalin; and halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone; sulphoxides such as dimethyl sulphoxide or sulphones such as sulpholane. Particular preference is given, for example, to tetrahydrofuran, acetonitrile, sulpholane, toluene, xylene, chlorobenzene, very particular preference is given, for example, to chlorobenzene, acetonitrile, and sulpholane.

According to another embodiment of the invention, a compound of the formula (IIa)

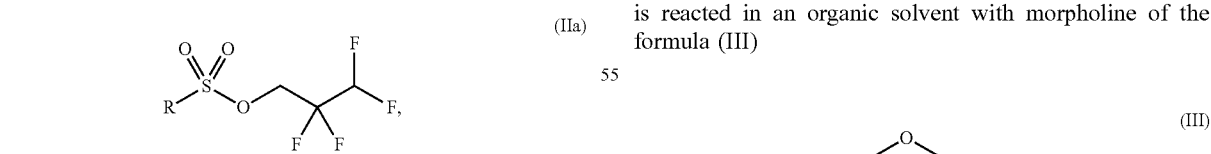

wherein
R represents $C_1$-$C_4$ alkyl, phenyl, or naphthyl,
where the phenyl is unsubstituted or substituted by one, two or three substituents independently of one another selected from the group consisting of linear or branched $C_1$-$C_4$ alkyl, chlorine, fluorine, bromine, amino, nitro, methylsulfonyl, (dimethyl-oxopropyl)amino, and sulfonic acid 2,2,3,3-tetrafluoropropylester, is reacted in an organic solvent with morpholine of the formula (III)

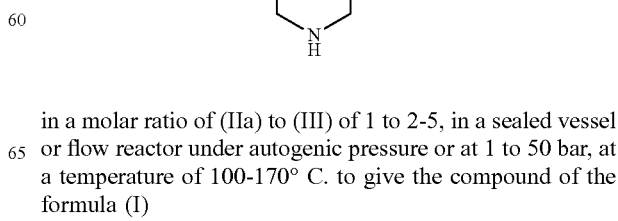

in a molar ratio of (IIa) to (III) of 1 to 2-5, in a sealed vessel or flow reactor under autogenic pressure or at 1 to 50 bar, at a temperature of 100-170° C. to give the compound of the formula (I)

and a compound of the formula (IVa)

wherein
R is as defined for the compounds of the formula (IIa).

According to another embodiment of the invention, the compound of the formula (II)

is reacted in an organic solvent with morpholine of the formula (III)

in a molar ratio of (IIa) to (III) of 1 to 2-5, in a sealed vessel or flow reactor under autogenic pressure or at 1 to 50 bar, at a temperature of 100-170° C. to give the compound of the formula (I)

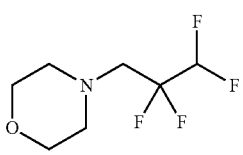

and the compound of the formula (IV)

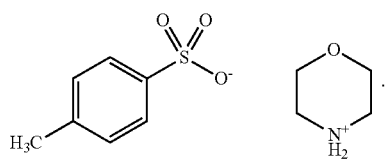

The reaction of compound (II) and morpholine according to the invention is effected at temperatures of 100-170° C., preferably at temperatures of 100-150° C., more preferably at 120-150° C.

The reaction is carried out in a sealed vessel or a flow reactor, and under autogenic pressure or at a pressure of 1 to 50 bar.

A sealed vessel within the meaning of the present invention is any sealable vessel that is suitable for the temperature and pressure according to the invention. According to one example, the sealed vessel is an autoclave.

A flow reactor within the meaning of the present invention is any flow reactor suitable for the temperature and pressure according to the invention.

Autogenic pressure within the meaning of the present invention is defined as the equilibrium pressure that is present during the reaction in a given sealed vessel or flow reactor at a given temperature and given amount of educts.

The process can be conducted as a batch or semi batch process. When conducting the process as a batch process all reactants and solvents are introduced in the reactor and the reaction is performed under the above mentioned conditions. When conducting the process as a semi batch process under the above mentioned conditions one of the reactants—either morpholine or the compound of formula (II) or (IIa)—is charged into the reactor and the second reactant—the compound of formula (II) or (IIa) or morpholine, respectively—is added over a period of time. Further dosing of both reactants morpholine and the compound of formula (II) or (IIa) can be performed simultaneously into a vessel or using a flow reactor.

For the work up, the sealed vessel or flow reactor is cooled to 20° C. to 80° C., the reaction mixture is diluted with an organic solvent, for example methyl tert-butyl ether, the salt of the formula (IV) or (IVa) is removed via filtration, access of morpholin and solvent are removed in vacuum, and the compound of the formula (I) is obtained by distillation.

Alternatively and preferably, the autoclave is cooled to 80° C. to 100° C., the reaction mixture is diluted with water, the product layer is separated and the aqueous layer is washed with an organic solvent, for example methyl tert-butyl ether. The compound of the formula (I), dissolved in organic solvent, is used without purification or is additionally purified by distillation.

EXAMPLE 1

The stirred mixture of 2,2,3,3-tetrafluoropropyltosylate of the formula (II) (10.0 g, 0.035 mol) and morpholine (6.08 g, 0.070 mol) was heated in autoclave for 5 h at 140° C. The autoclave was cooled to room temperature, opened and the reaction mixture was diluted with 75 ml methyltert.butyl ether (3×25 ml). The morpholine salt was filtered off and the filtrate was evaporated in vacuum (10-20 mm Hg) at 20-25° C. The compound of the formula (I) (4-(2,2,3,3-tetrafluoropropyl)morpholine) was obtained as colorless liquid by distillation under atmospheric pressure.

B.p. 165-168° C., yield 5.6 g (79%).

EXAMPLE 2

The stirred mixture of 2,2,3,3-tetrafluoropropyltosylate of the formula (II) (10.0 g, 0.035 mol) and morpholine (6.08 g, 0.070 mol) was heated in autoclave for 12 h at 120° C. The autoclave was cooled to room temperature, opened and the reaction mixture was diluted with 75 ml methyltert.butyl ether (3×25 ml). The morpholine salt was filtered off and the filtrate was evaporated in vacuum (10-20 mm Hg) at 20-25° C. The compound of the formula (I) (4-(2,2,3,3-tetrafluoropropyl)morpholine) was obtained as colorless liquid upon distillation under atmospheric pressure.

B.p. 165-168° C., yield 5.8 g (82.4%).

EXAMPLE 3

The stirred mixture of 2,2,3,3-tetrafluoropropyltosylate of the formula (II) (330.0 g, 1.10 mol) and morpholine (208.0 g, 2.39 mol) was heated in autoclave for 18 h at 130° C. The autoclave was cooled to 80° C., opened and the reaction mixture was diluted with 110 ml water and further cooled to room temperature. The lower product layer was separated and the aqueous layer was washed with methyltert.butyl ether (2×83 ml). The organic layers were combined and the solvent was evaporated at normal pressure. The compound of the formula (I) (4-(2,2,3,3-tetrafluoropropyl)morpholine) was obtained as colorless liquid upon distillation in vacuum 185 mm Hg at 115° C.

B.p. 115° C./185 mbar, yield 188.0 g (85%).

$^1$H-NMR (400 MHz, CDCl$_3$): δ=2.50-2.69 (m, 4H), 2.89 (tt, J=14.06, 1.83 Hz, 2H), 3.43-3.89 (m, 4H), 5.72-6.28 (m, 1H) ppm

The invention claimed is:

1. A process for preparing the compound of the formula (I)

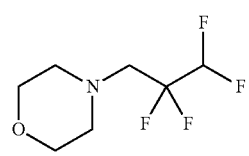

comprising reacting a compound of the formula (IIa)

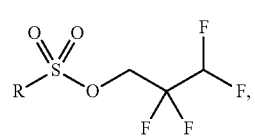

wherein

R represents $C_1$-$C_4$ alkyl, phenyl, or naphthyl,
where the phenyl is unsubstituted or substituted by one, two or three substituents independently of one another selected from the group consisting of linear or branched $C_1$-$C_4$ alkyl, chlorine, fluorine, bromine, amino, nitro, methylsulfonyl, (dimethyl-oxopropyl) amino, and sulfonic acid 2,2,3,3-tetrafluoropropyl-ester, in an organic solvent or without solvent with morpholine of the formula (III)

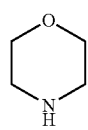
(III)

in a molar ratio of (IIa) to (III) of 1 to 2-5, in a sealed vessel or flow reactor under autogenic pressure or at 1 to 50 bar, at a temperature of 100-170° C. to give the compound of the formula (I)

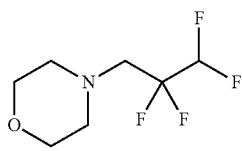
(I)

and a compound of the formula (IVa)

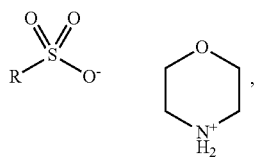
(IVa)

wherein

R is as defined for the compounds of the formula (IIa).

2. The process according to claim 1, wherein in the compound of the formula (IIa)

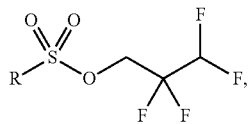
(IIa)

R represents methyl or phenyl,
where the phenyl is unsubstituted or substituted by one, two or three substituents independently of one another selected from the group consisting of methyl, chlorine, amino, methyl sulfonyl, and sulfonic acid 2,2,3,3-tetrafluoropropyl ester.

3. The process for preparing the compound of the formula (I)

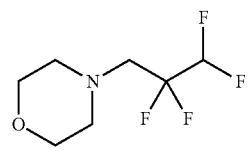
(I)

according to claim 1, wherein reacting the compound of the formula (IIa) comprises reacting the compound of the formula (II)

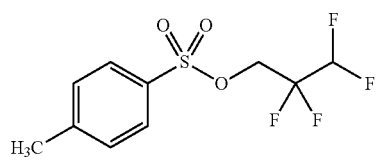
(II)

is reacted in an organic solvent or without solvent with morpholine of the formula (III)

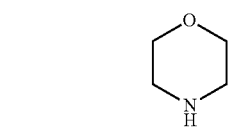
(III)

in a molar ratio of (II) to (III) of 1 to 2-5, in a sealed vessel or flow reactor under autogenic pressure or at 1 to 50 bar, at a temperature of 100-170° C. to give the compound of the formula (I)

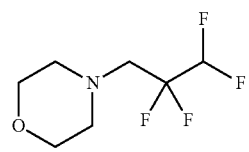
(I)

and the compound of the formula (IV)

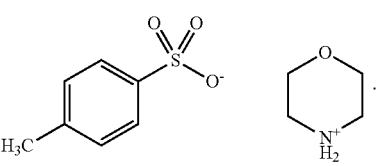
(IV)

4. The process for preparing the compound of the formula (I)

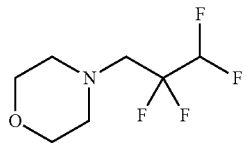

according to claim 1, wherein the reaction is carried out without solvent.

5. The process according to claims 1, wherein the molar ratio of the compound of formula (IIa) to the compound of formula (III) is 1 to 2.0-2.5.

6. The process according to claim 1, wherein the molar ratio of the compound of formula (IIa) to the compound of formula (III) is 1 to 2.1.

7. The process according to claim 1, wherein the reaction is effected at a temperature of 100-150° C.

8. The process according to claim 1, wherein the reaction is effected at a temperature of 120-150° C.

9. The process according to claim 1, wherein, after the reaction yielding the compounds of the formulae (I) and (IVa) is terminated, the process further comprises cooling the sealed vessel or flow reactor to 20° C. to 80° C., diluting the reaction mixture with an organic solvent, removing the salt of the formula (IVa) via filtration, removing excess of morpholine and solvent in vacuum, and obtaining the compound of the formula (I) by distillation.

10. The process according to claim 1, wherein, after the reaction yielding the compounds of the formulae (I) and (IVa) is terminated, the process further comprises cooling the sealed vessel or flow reactor to 80° C. to 100° C., diluting the reaction mixture with water, separating the product layer, washing the aqueous layer with an organic solvent, and using the compound of the formula (I), dissolved in organic solvent, without purification or additionally purifying the compound of the formula (I) by distillation.

* * * * *

UNITED STATES PATENT AND TRADEMARK OFFICE
CERTIFICATE OF CORRECTION

| | | |
|---|---|---|
| PATENT NO. | : 11,760,737 B2 | Page 1 of 1 |
| APPLICATION NO. | : 17/424866 | |
| DATED | : September 19, 2023 | |
| INVENTOR(S) | : Peter Fey et al. | |

It is certified that error appears in the above-identified patent and that said Letters Patent is hereby corrected as shown below:

In the Claims

Claim 3, Column 12, Line 27, "is reacted in" should be --in--.

Claim 5, Column 13, Line 14, "claims" should be --claim--.

Signed and Sealed this
Twenty-first Day of November, 2023

Katherine Kelly Vidal
*Director of the United States Patent and Trademark Office*